United States Patent [19]

Camenzind et al.

[11] Patent Number: 5,328,621
[45] Date of Patent: Jul. 12, 1994

[54] DITHIOPHOSPHATES AS ANTIWEAR ADDITIVES

[75] Inventors: Hugo Camenzind, Bern; Paul Dubs, Marly, both of Switzerland

[73] Assignee: Ciba-Geigy Corporation, Ardsley, N.Y.

[21] Appl. No.: 140,573

[22] Filed: Oct. 21, 1993

[30] Foreign Application Priority Data

Oct. 30, 1992 [CH] Switzerland .................. 3388/92

[51] Int. Cl.[5] .................................. C10M 137/04
[52] U.S. Cl. ........................... 252/46.6; 252/78.5; 558/162; 558/187
[58] Field of Search ............... 252/46.6; 558/162, 187

[56] References Cited

U.S. PATENT DOCUMENTS

| | | | |
|---|---|---|---|
| 4,153,562 | 5/1979 | Jaruzelski | 252/46.6 |
| 4,322,303 | 3/1982 | Rosenberger | 252/46.6 |
| 4,349,445 | 9/1982 | Rosenberger | 252/46.6 |
| 4,729,840 | 3/1988 | Lange et al. | 558/156 |
| 5,026,493 | 6/1991 | Lam et al. | 252/46.6 |

FOREIGN PATENT DOCUMENTS 8800589  1/1988  PCT Int'l Appl. .

OTHER PUBLICATIONS

Chem. Abst. 115 (18): 186461x (1991).

*Primary Examiner*—Jacqueline V. Howard
*Attorney, Agent, or Firm*—Luther A. R. Hall

[57] ABSTRACT

The invention relates to novel compounds of formulae I, II and III

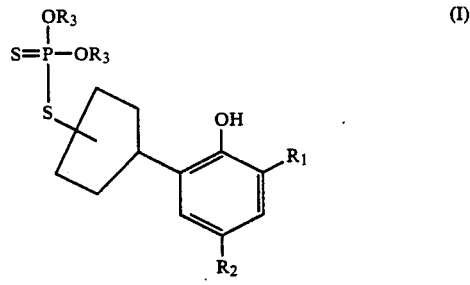

(I)

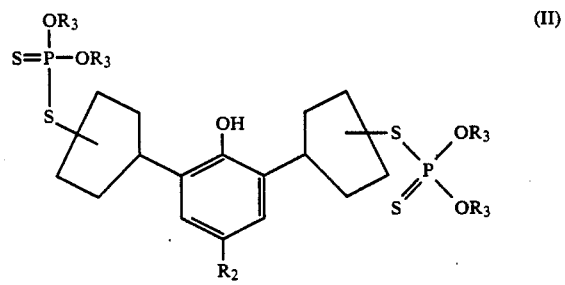

(II)

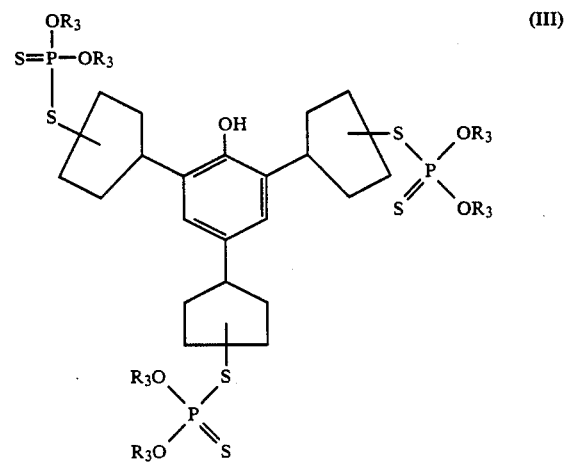

(III)

wherein $R_1$ is hydrogen, $C_1$–$C_{20}$alkyl or $C_5$–$C_7$cycloalkyl, $R_2$ is hydrogen, $C_1$–$C_{20}$alkyl or $C_5$–$C_7$cycloalkyl, and $R_3$ is $C_1$–$C_{18}$alkyl or $C_3$–$C_{18}$alkenyl. The compounds are used as antiwear additives for lubricants.

9 Claims, No Drawings

DITHIOPHOSPHATES AS ANTIWEAR ADDITIVES

The present invention relates to novel dithiophosphates and to compositions comprising a lubricant, a hydraulic fluid or a machining fluid and at least one such dithiophosphate.

The running of engines requires the moving metal parts to be lubricated. Especially in combustion engines the pressure and temperature conditions are extremely drastic and exacting demands are made of the lubricant.

Phosphorus- and sulfur-containing compounds have been found useful for ensuring the formation and maintenance of a lubricating film on the metal surfaces.

It is known to add to lubricants dithiophosphates which protect the moving metal parts from wear and tear and which themselves also contribute to the stabilisation of the lubricant. Zinc dialkyldithiophosphates are normally used. However, in modern combustion engines fitted with a catalytic converter, the metal content of these oil additives creates problems. Increased ash content can substantially shorten the life of the catalytic converter.

For this reason an intensified search is being made in industry to provide effective metal-free and hence ashless antiwear additives.

A further problem to be avoided is the corrosive action of the additive on copper and its alloys.

It is known to use reaction products of dihiophosphoric acids with alkenes, acrylic and maleic acid derivatives as additives for lubricating oils [S. B. Borshchevskii et al., Khim Tekhnolog. Topl. Masel (6) 24-6 (1991)].

Surprisingly, it has now been found that the compounds of formulae I, II and III described below are very suitable antiwear additives, especially for lubricating oils, and have scarcely any corrosive action on copper.

Accordingly, the invention relates to compounds of formula I, II or III

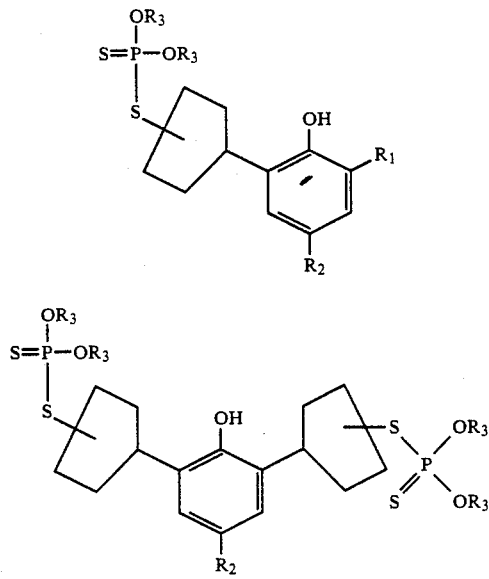

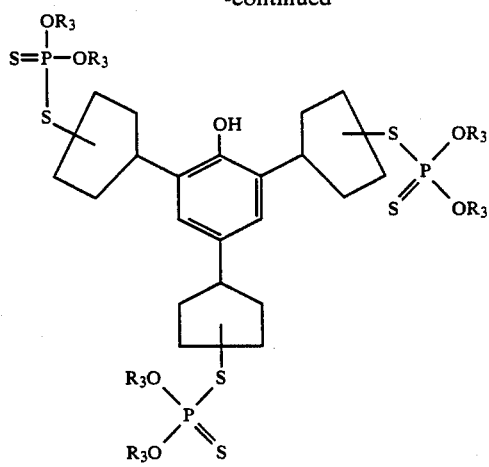

wherein
$R_1$ is hydrogen, $C_1$–$C_{20}$alkyl or $C_5$–$C_7$cycloalkyl,
$R_2$ is hydrogen, $C_1$–$C_{20}$alkyl or $C_5$–$C_7$cycloalkyl, and
$R_3$ is $C_1$–$C_{18}$alkyl or $C_3$–$C_{18}$alkenyl.

$R_1$ and $R_2$ defined as $C_{1-20}$alkyl may be straight- or branched-chain and are typically methyl (Me), ethyl, propyl, isopropyl (i-Pr), n-butyl, isobutyl (i-Bu), tert-butyl (t-Bu), pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1-methylundecyl or eicosyl.

$R_1$ and $R_2$ defined as $C_5$–$C_7$cycloalkyl are cyclopentyl, cyclohexyl and cycloheptyl.

$R_3$ as $C_3$–$C_{18}$alkenyl is also straight- or branched-chain and is typically allyl, 2-methallyl, 2-butenyl, 3-butenyl, isobutenyl, n-penta-2,4-dienyl, 3-methyl-but-2-enyl, hexenyl, n-oct-2-enyl, n-dec-2-enyl, n-dodec-2-enyl, isododecenyl, n-octadec-2-enyl, n-octadec-4-enyl, undecenyl, heptadecenyl or oleyl.

Preferably $R_1$ is hydrogen or $C_1$–$C_{12}$alkyl, $R_2$ is hydrogen or $C_1$–$C_{12}$alkyl and $R_3$ is $C_1$–$C_{12}$alkyl or $C_3$–$C_8$alkenyl.

Compounds of formula I are also preferred.

Particularly preferred compounds are those in which $R_1$ and $R_2$ are each independently of the other hydrogen or $C_1$–$C_{12}$alkyl and $R_3$ is $C_1$–$C_{12}$alkyl.

Most preferred are compounds of formula I, wherein $R_1$ and $R_2$ are hydrogen or $C_1$–$C_4$alkyl, and $R_3$ is $C_1$–$C_4$alkyl. In these compounds, at least one of $R_1$ and $R_2$ is preferably methyl.

The invention further relates to compositions comprising

A) a lubricant, a hydraulic fluid or a machining fluid, and

B) at least one compound of formula I, II or III. The compounds referred to above as preferred lead to correspondingly preferred compositions.

Those compositions are also preferred wherein component A) is a lubricant.

The function of the lubricant in the running of engines consists not only in the lubrication of the moving parts, but also in the protection of the stationary part in contact with the lubricant oil from e.g. wear and corrosion.

The compounds of formula I, II or III afford protection against wear and tear and will conveniently be present in the novel compositions in amounts of 0.01 to 10% by weight, typically 0.05 to 5% by weight, preferably 0.05 to 3% by weight and, most preferably, 0.1 to 2% by weight. The novel compositions may contain one or more than one of these compounds, and the percentages by weight are based on the total amount of said compounds. The basis of calculation is the total weight of the lubricant, machining fluid or hydraulic fluid without the compounds of formula I,II or III.

Mixtures of compounds of formula I, II or III can, of course, also be used.

The invention thus also relates to the use of compounds of formula I, II and III as additives for lubricants, hydraulic fluids and machining fluids, especially as extreme-pressure and antiwear additives. As the antiwear action is also crucial when using the lubricant, such a utility also entails a process for enhancing the performance properties of lubricants, hydraulic fluids and machining fluids, which process comprises adding thereto said compounds of formula I, II or III.

The suitable lubricants, hydraulic fluids and machining fluids are typically based on mineral or synthetic oils or mixtures thereof. The lubricants are known to the skilled person and are described in the relevant literature, inter alia in Dieter Klamann, "Schmierstoffe und verwandte Produkte" (Lubricants and Related Products) (Verlag Chemic, Weinheim, 1982), in Schewe-Kobek, "Das Schmiermittel-Taschenbuch" (Handbook of Lubricants) (Dr. Alfred Hüthig-Verlag, Heidelberg, 1974), and in "Ullmanns Enzyklopädie der technischen Chemie" (Ullmann's Encyclopedia of Industrial Chemistry), Vol. 13, pages 85–94 (Verlag Chemie, Weinheim, 1977).

The lubricants are preferably oils and fats and are typically derived from a mineral oil. Oils are preferred.

A further group of lubricants suitable for use in the practice of this invention comprises vegetable or animal oils, fats, tallows and waxes or mixtures with one another or with the mineral or synthetic oils referred to above. Vegetable and animal oils, fats, tallows and waxes are typically palm nut oil, palm oil, olive oil, beet oil, rapeseed oil, linseed oil, ground nut oil, soybean oil, cottonseed oil, sunflower seed oil, pumpkin seed oil, coconut oil, corn oil, castor oil, walnut oil and mixtures thereof, fish oils, the tallows of slaughter animals, e.g. beef tallow, neat's foot and bone oil, as well as the modified, epoxidised and sulfoxidised forms thereof, typically epoxidised soybean oil.

The mineral oils are based in particular on hydrocarbon compounds.

Synthetic lubricants typically comprise lubricants based on aliphatic or aromatic carboxylates, polymeric esters, polyalkylene oxides, phosphates, poly-$\alpha$-olefins or silicones, on a diester of a divalent acid with a monohydric alcohol, typically dioctyl sebacate or dinonyl adipate, on a triester of trimethylolpropane with a monovalent acid or with a mixture of acids, conveniently trimethylolpropane tripelargonate, trimethylolpropane tricaprylate or mixturtes thereof, on a tetraester of pentaerythritol with a monovalent acid or with a mixture of such acids, typically pentaerythritol tetracaprylate, or on a complex ester of monovalent and divalent acids with polyhydric alcohols, for example a complex ester of trimethylolpropane with caprylic and sebacic acid or of a mixture thereof. Especially suitable lubricants are, in addition to mineral oils, typically poly-$\alpha$-olefins, ester-based lubricants, phosphates, glycols, polyglycols and polyalkylene glycols and mixtures thereof with water.

Machining fluids and hydraulic fluids can be prepared from the same substances as those described above in connection with the lubricants. Often they are also emulsions of such substances in water or other liquids.

The lubricating compositions of this invention are used, inter alia, for combustion engines, typically for motor vehicles.

The compounds of formula I, II or III are readily soluble in lubricants, machining fluids and hydraulic fluids and are therefore especially suitable for use as additives for lubricants, machining fluids and hydraulic fluids. Their surprisingly good antiwear properties merit special mention.

The lubricants, machining fluids and hydraulic fluids of this invention may also contain other additives which are added for further enhancement of the basic properties. These further additives comprise antioxidants, metal deactivators, rust inhibitors, viscosity improvers, pour-point depressants, dispersants, detergents, other extreme-pressure and antiwear additives.

Illustrative examples of such further additives are:

Examples of phenolic antioxidants

1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol and 2,6-didodecylthiomethyl-4-nonylphenol.

3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis-(3,5-di-tert-butyl-4-hydroxyphenyl) adipate.

4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis-(6-tert-butyl-2-methylphenol), 4,4'-thiobis(3,6-di-sec-amylphenol) and 4,4'-bis-(2,6-di-methyl-4-hydroxyphenyl) disulfide.

5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis-(6-nonyl-4-methylphenol), 2,2'-methylenebis(4,6-di-tert-butylphenol), 2,2'-ethylidene-bis-(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha$,$\alpha$-dimethylbenzyl)-4-nonylphenol], 4,4'-methylenebis(2,6-di-tert-butylphenol), 4,4'-methylenebis(6-tert-butyl- 2- methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methylphenyl)dicyclopentadiene, bis[2-(3'-tert-butyl-2'hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4hydroxyphenyl)propane, 2,2-bis(5-tert-butyl-4-hydroxy-2-methylphenyl)-4-n-dodecylmercaptobutane and 1,1,5,5-tetra(5-tert-butyl-4-hydroxy-2-methylphenyl)pentane.

6. O-, N- and S-Benzyl compounds, for example 3,5,3', 5'-tetra-tert-butyl-4,4'-dihydroxydibenzyl ether, octadecyl 4-hydroxy-3,5-dimethylbenzyl-mercaptoacetate, tris(3,5-di-tert-butyl-4-hydroxybenzyl)amine, bis(4-tert-butyl-3-hydroxy-2,6-dimethylbenzyl)-dithioterephthalate, bis(3,5-di-tert-butyl-4-hydroxybenzyl) sulfide and isooctyl 3,5-di-tert-butyl-4-hydroxybenzylmercaptoacetate.

7. Hydroxybenzylated malonates, for example dioctadecyl 2,2-bis(3,5-di-tert-butyl-2-hydroxybenzyl)malonate, dioctadecyl 2(3-tert-butyl-4-hydroxy-5-methylbenzyl)malonate, didodecylmercaptoethyl 2,2-bis(3,5-di-tert-butyl-4-hydroxybenzyl)malonate and bis[4-(1,1,3,3-tetramethylbutyl)phenyl]2,2-bis(3,5-di-tert-butyl-4-hydroxybenzyl)malonate.

8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene and 2,4,6-tris(3,5-di-tert-butyl-4-hydroxybenzyl)phenol.

9. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine and 1,3,5-tris(3,5-di-cyclohexyl-4-hydroxybenzyl)isocyanurate.

10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl- 4-hydroxybenzylphosphonate, dioctadecyl 5-tert-butyl-4-hydroxy-3-methylbenzylphosphonate and the calcium salt of monoethyl 3,5-di-tert-butyl-4-hydroxybenzylphosphonate.

11. Acylaminophenols, for example 4-hydroxylauranilide, 4-hydroxystearanilide and octyl N-(3,5-di-tert-butyl-4-hydroxyphenyl)carbamate.

12. Esters of β-(3,5-di-tert-butyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

13. Esters of β-(5-tert-butyl-4-hydroxy-3-methylphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

14. Esters of β-(3,5-dicyclohexyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

16. Amides of β-(3,5-di-tert-butyl-4-hydroxyphenyl)-propionic acid, for example N,N'-bis( 3,5-di-tert-butyl-4-hydroxyphenylpropionyl)hexamethylenediamine, N,N'-bis(3,5-di-tert-butyl-4-hydroxyphenylpropionyl)-trimethylenediamine and N,N'-bis(3,5-di-tert-butyl-4-hydroxyphenylpropionyl)hydrazine.

Examples of aminic antioxidants

N,N'-diisopropyl-p-phenylenediamine, N,N'-di-sec-butyl-p-phenylenediamine, N,N'-bis-(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methyl-phenyl)amino]ethane, 1,2-bis(phenylamino)propane, (o-tolyl)biguanide, bis[4-(1', 3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpipefidin-4-ol.

Examples of other antioxidants

Aliphatic or aromatic phosphites, esters of thiodipropionic acid or of thiodiacetic acid, or salts of dithiocarbamic or dithiophosphofic acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)aminomethyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutriazole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[-di(2-ethylhexyl)aminomethyl]-1,3,4-thiadiazolin-2-one.

e) Amino compounds, for example salicylidenepropylenediamine, salicylaminoguanidine and salts thereof.

Examples of rust inhibitors are a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:

I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.

II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)glycerols, 1-(alkylphenoxy)-3-(2,3-dihydroxypropyl)glycerols and 2-carboxyalkyl-1,3-dialkylglycerols.

Examples of viscosity index improvers are

Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are

Polymethacrylate and alkylated naphthalene derivatives.

Examples of dispersants/surfactants are

Polybutenylsuccinic amides or -imides, polybutenylphosphonic acid derivatives and basic magnesium, calcium and barium sulfonates and phenolates.

Examples of antiwear additives are

Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl )thio]propionate, triphenyl thiophosphate (triphenylphosphorothioate), tris(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole such as 1-[N,N-bis(2-ethylhexyl)aminomethyl]-2-mercapto-1H-1,3-benzothiazole, and ethoxycarbonyl-5-octyldithiocarbamate.

The compounds of this invention are prepared by per se known methods by addition of O,O-diesters of dithiophosphoric acid to (2-cyclopenten-1-yl)phenols, as exemplified in the case of the compounds of formula I:

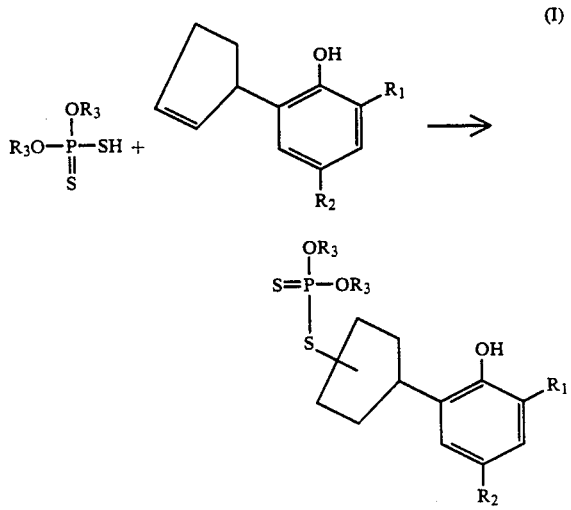

The compounds of formulae II and III can be prepared from the corresponding 2-cyclopenten-1-yl-di- or trisubstituted phenols with 2 or 3 equivalents of thiophosphoric acid.

The preferred procedure is in general accordance with standard methods of adding mercaptans to olefins as described, inter alia, in Organikum, p. 343. In Houben Weyl, Methoden der Organischen Chemie, Vol. XII/2, p. 709 ff. it is stated, inter alia:

"When carrying out the addition of O,O-diesters of dithiophosphoric acid to olefinic compounds, the general procedure comprises heating stoichiometric amounts of the components to temperatures in the range from 50° to 100° C. until the degree of acidity no longer decreases. The reactions are often exothermic and may, if desired, be controlled by addition of a solvent. It is sometimes advisable to add basic substances such as alkalies or tertiary amines (triethylamine, picoline and the like)."

It is preferred to carry out the reaction without a solvent, but if necessary a solvent may be used. The reaction normally does not require a catalyst, but it can be accelerated with e.g. azoisobutyronitrile. The temperature range is conveniently from 60° to 120° C. The reaction times will depend on the size of the batch and the further reaction conditions, but on a laboratory scale are normally from 6 to 20 hours.

(2-Cyclopenten-1-yl)phenols can be obtained by known methods, inter alia as described in U.S. Pat. No. 3,689,573. This reference describes in particular 2-cyclopentene-mono- and disubstituierte phenols. The Friedel-Crafts reaction is accelerated by catalysts such as aluminium compounds or zeolites. Cyclopentadiene is used in commercially available dimeric form. A c. 5-fold molar excess of cyclopentadiene gives a mixture consisting about 60% of the trisubstituted 2,4,6-(2-cyclopenten-1-yl)phenol. Standard (e.g. chromatographic) separation methods give the pure product that can be reacted with the O,O-diester of dithiophosphoric acid. The appropriate O,O-diesters of dithiophosphoric acid are commercially available or can be prepared by known methods.

The following Examples illustrate the invention in more detail. Unless otherwise indicated, all pans and percentages are by weight.

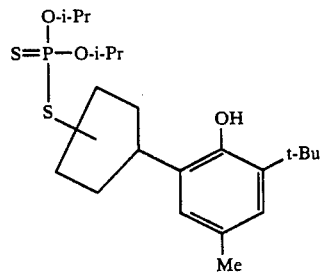

EXAMPLE 1

Under nitrogen, 23.5 g (0.1 mol) of 2-tert-butyl-6-(2-cyclopenten-1-yl)-4-methylphenol and 22.1 g (0.1 mol) of diisopropyldithiophosphoric acid are heated over 15 min to 100° C. and stirred for 15 hours at this temperature. The crude product is purified over a flash chromatography column on 600 g of silica gel with hexane/ethyl acetate (19:1). The solvent is then distilled off, giving 30.7 g of an orange oil (69% of theory). Refractive index and analysis as reported in Table I.

EXAMPLES 2-10

Following the same procedure as described in Example 1, the compounds of Examples 2-10 are prepared from the appropriately substituted (2-cyclopenten-1-yl)phenols and diisopropyldithiophosphoric acid or diisobutyldithiophosphoric acid. Compounds of formulae II and III are prepared using 2 and 3 equivalents, respectively, of the appropriate dithiophosphoric acid. Properties and analytical data of the resultant compounds of formulae I, II and III are listed in Table I.

EXAMPLE 11: TEST FOR ANTIWEAR PROTECTION

The test for suitability as antiwear additive is carried out by ASTM standard method D-2783-81 using the Shell 4-ball apparatus. The base oil used is STOCK 305 sold by Mobil, to which the amount of compound indicated in Table II is added in accordance with each Example. The average WSD (wear scar diameter) is measured at a load of 20 kg after a 1 hour operation at 60° C. (in mm). The results are reported in Table II.

EXAMPLE 12: TEST FOR CORROSIVE ACTION ON COPPER

The corrosive action on copper is tested in accordance with ASTM standard method D-130. A polished strip of copper is immersed for 3 hours in a sample composition kept for 3 hours at 120° C. This composition consists of the base oil described in Example 11 additionally containing 0.03% of the commercially available copper passivator (2-ethylhexyl)-aminomethyltolutriazole and, with the exception of the comparison sample, 1% of novel compound. The copper strip is removed from the oil, cleaned and evaluated using the ASTM Copper Strip Corrosion Standards. The evaluation is made in four steps:
1—no tarnish
2—moderate tarnish
3—strong tarnish
4—corrosion,
while additionally making a fine subdivision within the rating 1-4 on the basis of the shadowing on the specimens. In the qualitative evaluation A to E, the rating A comes before B and B before C etc.

The results obtained with 1% solutions of the respective novel compounds in the above described base oil are summarised in Table III.

TABLE I

| Example/ Formula | $R_1$ | $R_2$ | $R_3$ | Appearance | $n_D^{20}$ | Analysis calcd found | | | |
|---|---|---|---|---|---|---|---|---|---|
| | | | | | | C | H | S | P |
| 1/I | t-Bu | Me | i-Pr | orange yellow oil | 1.5436 | 59.43 | 8.39 | 14.42 | 6.97 |
| | | | | | | 58.90 | 8.57 | 14.94 | 7.14 |
| 2/I | t-Bu | Me | i-Bu | yellow viscous oil | 1.5396 | 60.98 | 8.74 | 13.57 | 6.55 |
| | | | | | | 61.02 | 8.83 | 13.39 | 6.55 |

TABLE I-continued

| Example/ Formula | $R_1$ | $R_2$ | $R_3$ | Appearance | $n_D^{20}$ | Analysis calcd found | | | |
|---|---|---|---|---|---|---|---|---|---|
| | | | | | | C | H | S | P |
| 3/I | Me | H | i-Pr | greenish-grey oil | 1.5591 | 55.65 | 7.52 | 16.50 | 7.97 |
| | | | | | | 55.67 | 7.55 | 16.38 | 8.09 |
| 4/I | Me | H | i-Bu | green oil | 1.5508 | 57.67 | 7.99 | 15.39 | 7.44 |
| | | | | | | 57.69 | 8.01 | 15.54 | 7.38 |
| 5/I | H | Me | i-Pr | brown viscous oil | 1.5649 | 55.64 | 7.52 | 16.51 | 7.97 |
| | | | | | | 55.75 | 7.24 | 16.92 | 8.18 |
| 6/I | H | Me | i-Bu | yellow oil slightly viscous | 1.5536 | 57.66 | 7.98 | 15.39 | 7.44 |
| | | | | | | 57.92 | 7.70 | 15.69 | 7.53 |
| 7/II | — | Me | i-Pr | brown viscous oil | 1.5600 | 52.07 | 7.53 | 19.17 | 9.26 |
| | | | | | | 53.79 | 7.16 | 18.34 | 8.72 |
| 8/II | — | Me | i-Bu | greenish yellow viscous oil | 1.5520 | 54.67 | 8.06 | 17.69 | 8.54 |
| | | | | | | 54.80 | 8.07 | 17.79 | 8.57 |
| 9/III | — | — | i-Pr | brown highly viscous oil | 1.5609 | 50.08 | 7.44 | 20.57 | 9.94 |
| | | | | | | 51.07 | 7.38 | 20.32 | 9.66 |
| 10/III | — | — | i-Bu | dark yellow viscous oil | 1.5512 | 53.02 | 8.01 | 18.87 | 9.11 |
| | | | | | | 53.96 | 7.79 | 18.41 | 9.05 |

TABLE II

| Compound of Example | Amount added | WSD [mm] |
|---|---|---|
| 1 | 1.0 | 0.44 |
| 1 | 0.25 | 0.58 |
| 2 | 1.0 | 0.45 |
| 2 | 0.25 | 0.76 |
| 3 | 1.0 | 0.31 |
| 3 | 0.25 | 0.41 |
| 4 | 1.0 | 0.41 |
| 4 | 0.25 | 0.41 |
| 5 | 1.0 | 0.30 |
| 5 | 0.25 | 0.37 |
| 6 | 1.0 | 0.31 |
| 6 | 0.25 | 0.40 |
| 7 | 1.0 | 0.38 |
| 7 | 0.25 | 0.41 |
| 8 | 1.0 | 0.38 |
| 8 | 0.25 | 0.37 |
| 9 | 1.0 | 0.33 |
| 9 | 0.25 | 0.41 |
| 10 | 1.0 | 0.40 |
| 10 | 0.25 | 0.43 |
| none | | 0.82 |

TABLE III

| Compound of Example | Corrosive action |
|---|---|
| 1 | 1B |
| 2 | 1B |
| 3 | 1B |
| 4 | 1B |
| 5 | 1B |
| 6 | 1B |
| 7 | 1B |
| 8 | 1B |
| 9 | 1B |
| 10 | 1B |
| none | 3B |

What is claimed is:

1. A compound of formula I, II or III

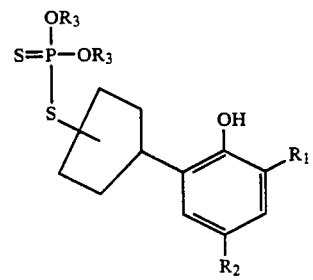  (I)

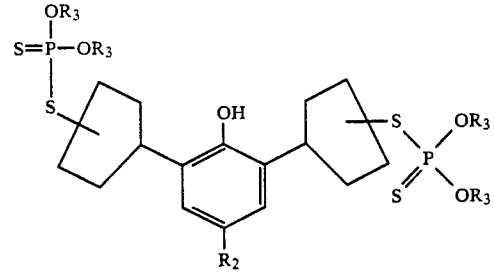  (II)

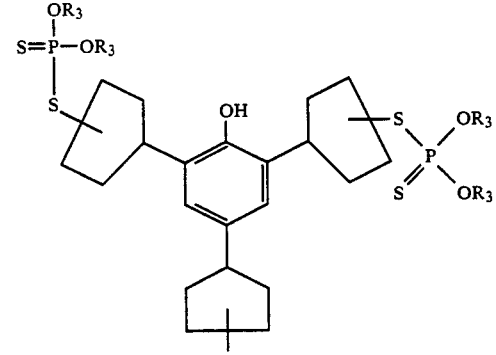  (III)

wherein
$R_1$ is hydrogen, $C_1$–$C_{20}$alkyl or $C_5$–$C_7$cycloalkyl,
$R_2$ is hydrogen, $C_1$–$C_{20}$alkyl or $C_5$–$C_7$cycloalkyl, and
$R_3$ is $C_1$–$C_{18}$alkyl or $C_3$–$C_{18}$alkenyl.

2. A compound of formula I according to claim 1.

3. A compound according to claim 1, wherein $R_1$ is hydrogen or $C_1$–$C_{12}$alkyl, $R_2$ is hydrogen or $C_1$–$C_{12}$alkyl and $R_3$ is $C_1$–$C_{12}$alkyl or $C_3$–$C_8$alkenyl.

4. A compound according to claim 1, wherein $R_1$ and $R_2$ are each independently of the other hydrogen or $C_1$–$C_{12}$alkyl and $R_3$ is $C_1$–$C_{12}$alkyl.

5. A compound according to claim 4, wherein $R_1$ and $R_2$ are hydrogen or $C_1$–$C_4$alkyl, and $R_3$ is $C_1$–$C_4$alkyl.

6. A composition comprising
   A) a lubricant, a hydraulic fluid or a machining fluid, and
   B) at least one compound of formula I, II or III according to claim 1.

7. A composition according to claim 6, wherein component A) is a lubricant.

8. A composition according to claim 7, which additionally comprises further stabilisers selected from the group consisting of antioxidants, anti-corrosion agents, metal deactivators, viscosity index improvers, dispergants, extreme-pressure and antiwear additives and pour-point depressants.

9. A process for enhancing the performance properties of lubricant compositions, hydraulic fluids and machining fluids, which comprises adding thereto a compound of formula I, II or III according to claim 1.

* * * * *